United States Patent
Su et al.

(10) Patent No.: US 7,815,310 B2
(45) Date of Patent: Oct. 19, 2010

(54) ADAPTIVE SEQUENTIAL WAVEFRONT SENSOR AND ITS APPLICATIONS

(75) Inventors: Wei Su, Sunnyvale, CA (US); Yan Zhou, Pleasanton, CA (US)

(73) Assignee: Clarity Medical Systems, Inc., Pleasanton, CA (US)

(*) Notice: Subject to any disclaimer, the term of this patent is extended or adjusted under 35 U.S.C. 154(b) by 390 days.

(21) Appl. No.: 11/761,890

(22) Filed: Jun. 12, 2007

(65) Prior Publication Data
US 2008/0278683 A1 Nov. 13, 2008

Related U.S. Application Data

(63) Continuation of application No. 11/335,980, filed on Jan. 20, 2006, now Pat. No. 7,445,335.

(51) Int. Cl.
*A61B 3/10* (2006.01)
(52) U.S. Cl. .................. 351/205; 351/211
(58) Field of Classification Search .......... 351/205, 351/211
See application file for complete search history.

(56) References Cited

U.S. PATENT DOCUMENTS

| | | | |
|---|---|---|---|
| 4,141,652 A | 2/1979 | Feinleib | |
| 5,164,578 A | 11/1992 | Witthoft | |
| 5,568,208 A | 10/1996 | Van de Velde | |
| 5,777,719 A | 7/1998 | Williams | |
| 6,199,986 B1 | 3/2001 | Williams | |
| 6,376,819 B1 | 4/2002 | Neal | |
| 6,685,317 B2 | 2/2004 | Su | |
| 6,791,696 B1 | 9/2004 | Fantone | |
| 6,964,480 B2 | 11/2005 | Levine | |

(Continued)

OTHER PUBLICATIONS

Dave, T., "Wavefront aberrometry Part 1: Current Theories and Concepts", Optometry Today, Nov. 19, 2004, pp. 41-45.
Ginis, H.S. et al., Variability of wavefront aberration measurments in small pupil sizes using a clinical Shack-Hartmann aberrometer, BMC Ophthalmology, Feb. 11, 2004, 4:1 copyright 2004 Ginis et al.

(Continued)

*Primary Examiner*—Joseph Martinez
*Assistant Examiner*—James R Greece
(74) *Attorney, Agent, or Firm*—Charles Krueger

(57) ABSTRACT

An adaptive sequential wavefront sensor comprises a sub-wavefront focusing lens, a sequential wavefront scanning device, a variable aperture, a position sensing device, and means for coordinating the operation of the wavefront scanning device, the variable aperture and the position sensing device. An adaptive sequential wavefront sensing method comprises the steps of sequentially projecting portions of a wavefront as image spots on a position sensing device, determining the deflection of each received image spot from a reference point on the position sensitive device, and coordinating the operation of a variable aperture with the operation the sequential projection and image position sensing. The adaptive sequential wavefront sensor has high speed, large dynamic range and variable spatial resolution, and hence can be used for real time measurement of the dynamics of eye accommodation. In addition, other functions or measurements can be combined with the adaptive sequential wavefront sensor to provide additional advantages. These additional function or measurement modules include a micro display based internal fixation and visual acuity projection module, a corneal topography module, and an optical coherence tomography module. When one or more of these modules is (are) combined with the adaptive sequential wavefront sensor, the combination system or apparatus can provide more accurate objective and subjective auto-refraction prescription, LASIK corneal ablation prescription, and contact lens or intra ocular lens prescriptions.

8 Claims, 9 Drawing Sheets

U.S. PATENT DOCUMENTS

| | | | |
|---|---|---|---|
| 2002/0169441 A1* | 11/2002 | Lemberg | 606/5 |
| 2003/0053031 A1 | 3/2003 | Wirth | |
| 2004/0004696 A1 | 1/2004 | Davis | |
| 2004/0156015 A1* | 8/2004 | Campbell | 351/205 |
| 2005/0134851 A1 | 6/2005 | Murphy | |

OTHER PUBLICATIONS

Liang, J. et al., Objective measurements of wave aberrations of the human eye with the use of a Hart-Shackman wave-front sensor, J. Opt. Soc. AM. A., vol. 11, No. 7, Jul. 1994, pp. 1949-1957, copyright 1994 Optical Society of America.

* cited by examiner

ADAPTIVE SEQUENTIAL WAVEFRONT SENSOR AND ITS APPLICATIONS

RELATED APPLICATIONS

This patent is a continuation of a patent application entitled "SEQUENTIAL WAVEFRONT SENSOR", application Ser. No. 11/335,980, filed Jan. 20, 2006 now U.S. Pat. No. 7,445,335 which is hereby incorporated by reference for all purposes.

BACKGROUND OF THE INVENTION

Currently, most wavefront sensors designed for measuring the aberration of a human eye involve the use of a two dimensional lenslet array and a two dimensional photodetector array such as a CCD or CMOS image sensor (U.S. Pat. Nos. 5,777,719, 6,530,917) for wavefront information collection. One problem associated with these wavefront sensors is the cross talk between neighboring sub-wavefronts sampled, which puts a limit to the wavefront spatial resolution. In an attempt to increase the wavefront resolution, a Talbot type wavefront sensor was recently introduced to the market which uses a cross grating and a CCD or CMOS detector array placed at the self-imaging plane of the cross grating (U.S. Pat. No. 6,781,681) to extract the wavefront information. Nevertheless, a common problem associated with these parallel simultaneous multiple sub-wavefront sensing schemes is the invariability of the grid associated with either the lenslet array or the diffraction grating and/or the photosensitive pixels of the CCD or CMOS sensor. Other drawbacks of these schemes include the relatively low data transfer rate resulting from the limited frame rate of the CCD or CMOS used and the time-consuming data processing required in order to extract the various orders of aberrations in the form of the coefficients of a Zernike polynomials. The fixedness of the grid and the relatively low speed of operation of these wavefront sensors put limitations to their applications. Although another technology based on laser beam tracing does not require the use of a two dimensional detector array for wavefront information extraction as described in U.S. Pat. No. 6,932,475, this patent did not discuss the speed and grid size issue.

In a pending patent application entitled "SEQUENTIAL WAVEFRONT SENSOR" (application Ser. No. 11/335,980), a high speed sequential wavefront sensor was disclosed that includes a variable aperture for controlling the size of each sampled sub-wavefront. However, no detailed elaboration has been given to describe how this aperture variability can be explored to bring additional advantages for different applications.

TECHNICAL FIELD

Figure 1:
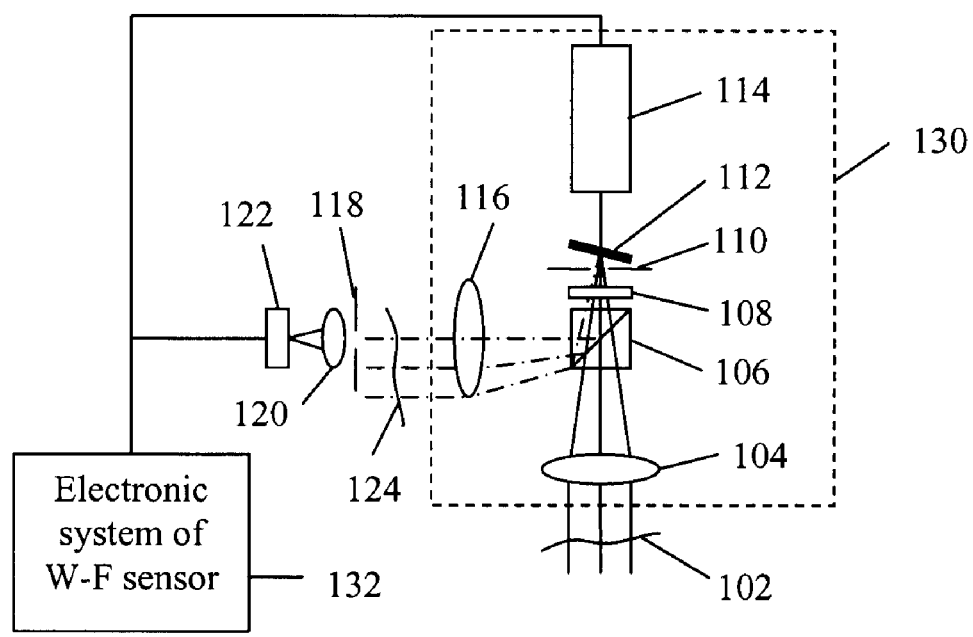
FIG. 1 shows a sequential wavefront sensor comprising a sub-wavefront focusing lens, a sequential wavefront scanning device, a variable aperture, and a position sensing device.

The present disclosure relates generally to a sequential wavefront sensor controllable to provide high speed, large dynamic range, and variable spatial resolution that can be combined with other measurement modules.

DESCRIPTION OF EXAMPLE EMBODIMENTS
OVERVIEW

The invention will now be described with reference to specific embodiments by way of example not limitation. In the drawings like or similar parts in different views have the same reference number. In the following embodiments of the invention are described that facilitate the use of the sequential wavefront sensor with other measurement modules. However, it will be apparent that the invention has general utility in many other environments.

DESCRIPTION

Reference will now be made in detail to various embodiments of the invention. Examples of these embodiments are illustrated in the accompanying drawings. While the invention will be described in conjunction with these embodiments, it will be understood that it is not intended to limit the invention to any embodiment. On the contrary, it is intended to cover alternatives, modifications, and equivalents as may be included within the spirit and scope of the invention as defined by the appended claims. In the following description, numerous specific details are set forth in order to provide a thorough understanding of the various embodiments. However, the present invention may be practiced without some or all of these specific details. In other instances, well known process operations have not been described in detail in order not to unnecessarily obscure the present invention.

FIG. 1 shows the sequential wavefront sensor that was disclosed in a pending patent application entitled "SEQUENTIAL WAVEFRONT SENSOR" (application Ser. No. 11/335,980). It comprises a light beam scanning module 130, an aperture 118, a sub-wavefront focusing lens 120, a detector with more than one photosensitive area 122 and a processor for calculating the sequentially obtained centroids of the sub-wavefronts to determine the aberration of the input wavefront. In particular, the sub-wavefront focusing lens 120 and the detector 122 are fixed in space and the input beam is scanned by the light beam scanning module 130 to sequentially project different portions of the input wavefront or a replica of the wavefront to the sub-wavefront focusing lens 120 and the detector 122. In this pending patent application, it has also been mentioned that the size of the sub-wavefront being sampled can be varied by controlling the size of the aperture 118. With further improvement, such a wavefront sensor can be made more adaptive to provide a number of additional advantages to a number of applications.

We will now discuss the advantages that one can further obtain by turning the sequential wavefront sensor into an adaptive one. Note that since the sampling of each sub-wavefront is sequential, they are separated in time and consequently, there is no longer the concern of a cross talk between neighboring sub-wavefronts as would happen for the simultaneous parallel sensing format when the tilting of a sub-wavefront is significant. Although in the parallel case, larger lenslet grid size can reduce cross talk, it will reduce the spatial resolution as well. In the adaptive sequential case, the aperture size for a sub-wavefront to be sampled by the adaptive sequential wavefront sensor can be made either large to achieve a desired high light sensitivity, adequate resolution and sub-wavefront averaging effect or as small as the diffraction limit allows, to substantially increase the spatial resolution as needed. The small aperture and hence high spatial resolution is especially beneficial for precision measurement of certain high order aberrations which, in the case of a human eye, are more predominant when the iris is widely open or in older patients.

On the other hand, the larger aperture will allow more averaging effect for higher order aberrations and faster data processing in exchange for the lower spatial resolution. In the case of a human eye, the aperture can be opened more for the central regions of the eye. Furthermore, for an adaptive sequential wavefront sensor, the photodetector used is typically a quadrant detector or in general a light spot position sensing device having a number of light sensing areas with parallel output ports. Such a detector brings two more advantages. The first one is its high speed and the second one is its larger dynamic range for light detection. For the adaptive sequential wavefront sensor, there are at least a number of electronic switching techniques to sequentially sample different sub-wavefronts. For example, if the light intensity or optical power from the light source is not a limitation, the light source that generates the wavefront to be sensed can be turned on continuously with a relatively high output power and an electronic shutter can be implemented for the quadrant detector. In this case, the wavefront scanning module can perform the scanning operation continuously. By turning the electronic shutter of the quadrant detector on and off for a desired pulse duration and repetition rate, a multiple number of sub-wavefronts can be sampled.

On the other hand, if there is a limit to the amount of light that can be used in terms of peak power, or optical energy, or average optical power as for the case of human eye aberration measurement, the light source used to create the wavefront can be pulsed or operated in burst mode at high speed in synchronization with the quadrant detector while the wavefront scanning module can be operated continuously. Since the light source and the quadrant detector both are much faster than a CCD, which will be limited by its frame rate, the only possible limitation to the sampling speed of an adaptive sequential wavefront sensor may come from the wavefront scanning module. If the wavefront scanning module is operated in a stepped fashion, it may be relatively slow. However, if it is operated in continuous mode, it can be fast enough for many applications. At present, MEMS based scanning mirrors or galvanometer scanners can operate at several kHz, while a typical CCD camera has a frame rate of only several tens of frames per second. High frame rate CCD or CMOS cameras are available but this would mean increased noise, and also a much higher price. In general, the sequential wavefront sensor can operate orders of magnitude faster than a typical parallel type wavefront sensor, not to mention the use of any electro-optical beam scanning device that can provide even higher beam scanning speed.

As for the dynamic range, a typical CCD only has 8 to 12 bits of data range and hence its dynamic range is limited to only 256 to 4096. A quadrant detector has four parallel channels with each channel capable of detecting signals with a dynamic range many orders of magnitude larger than a CCD. By selecting a proper optical power from the light source, this substantially improved dynamic range can lead to much higher resolution/precision for aberration measurement, enabling high precision sensing of tiny difference for each aberration mode.

Figure 2:
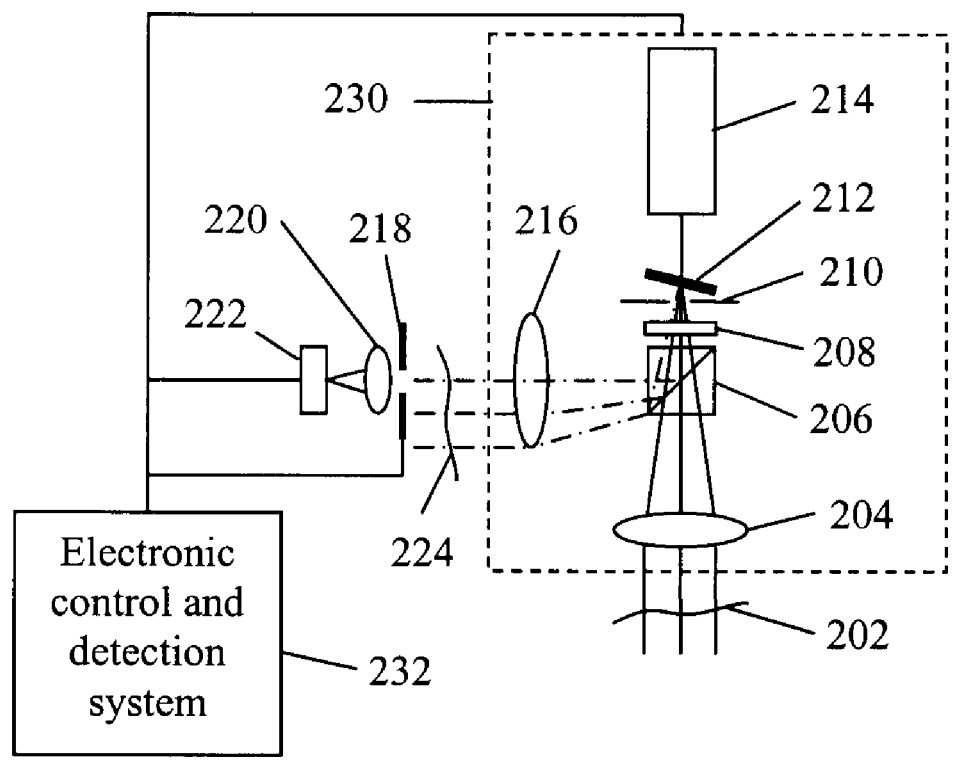
FIG. 2 shows an adaptive sequential wavefront sensor in which the operation of the wavefront scanning module, the variable aperture and the quadrant detector, are coordinated.

The above-mentioned advantages can be exploited for a number of applications. In one embodiment, as shown in FIG. 2, the operation of the wavefront scanning module 230, the variable aperture 218, and the quadrant detector 222, is coordinated. Electrical wires are connected to the three devices and their synchronization is monitored and controlled by the electronic control and detection system 232. By synchronizing the operation of these devices, the wavefront sampling speed, the spatial resolution, and the sampling pattern can all be controlled. In particular, for the measurement of a certain order of wavefront aberration, the number, size and scan pattern of the sub-wavefronts to be sampled can be optimized, which can result in a substantial reduction in the time required and the amount of data processed to calculate the magnitude of that particular order of wavefront aberration, in a manner similar to narrow band filtering or lock-in detection of an electronic signal. In the example of an eye, lower order aberrations are predominant when the iris opening is small while higher order aberrations contribute more to the drop in optical performance when the iris is wide open.

Therefore a dynamic adaptive sub-wavefront sampling approach can be adopted, in which the sub-wavefront aperture size for the central portion of the input wavefront can be made larger by opening the variable aperture more and the sub-wavefront aperture size for the outer portion of the input wavefront can be made smaller by reducing the size of the aperture opening. The density of the sampling points could also be increased for the outer portion by sampling at higher data rates. Since in most cases the input wavefront is circular, a polar coordinate based scanning will be advantageous. The scanning pattern can be in the form of a number of annular rings or a spiral or a number of radial spikes or others. Various scanning patterns can be programmed into the electronic control and detection system 232.

Note that in terms of system configuration, the variable aperture 218 does not need to be arranged in the front of the sub-wavefront focusing lens 220 and it can be arranged behind it or anywhere before the detector 222 as long as it can serve the purpose of controlling the size of the sub-wavefront being sampled and projected to the detector 222. Meanwhile it should also be understood that the word "coordination" should be interpreted in a broader sense to include the case in which the opening of the aperture remains unchanged.

Figure 3A:
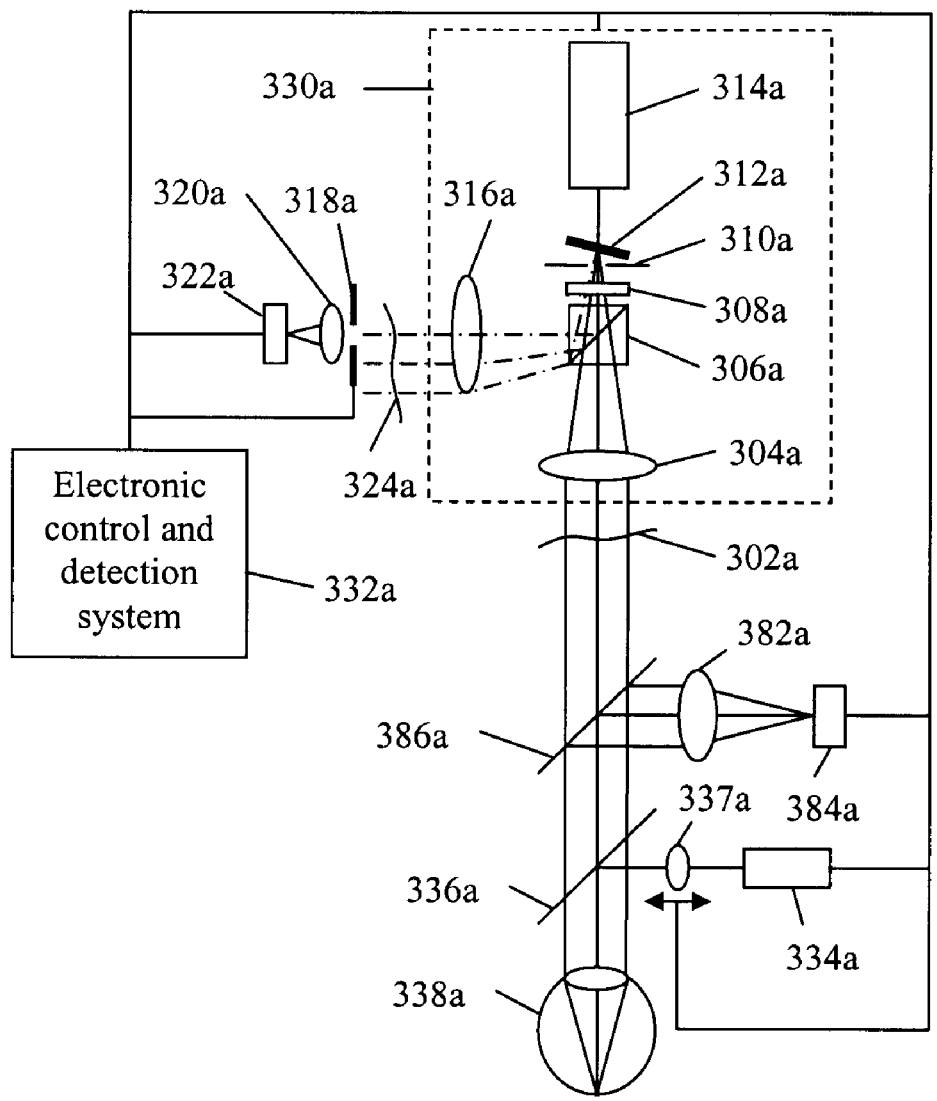
FIGS. 3a, b, and c show an adaptive sequential wavefront sensor for sensing the wavefront from an eye, in which the operation of the light source, the wavefront scanning module, the variable aperture and the quadrant detector, are coordinated.
Figure 3B:
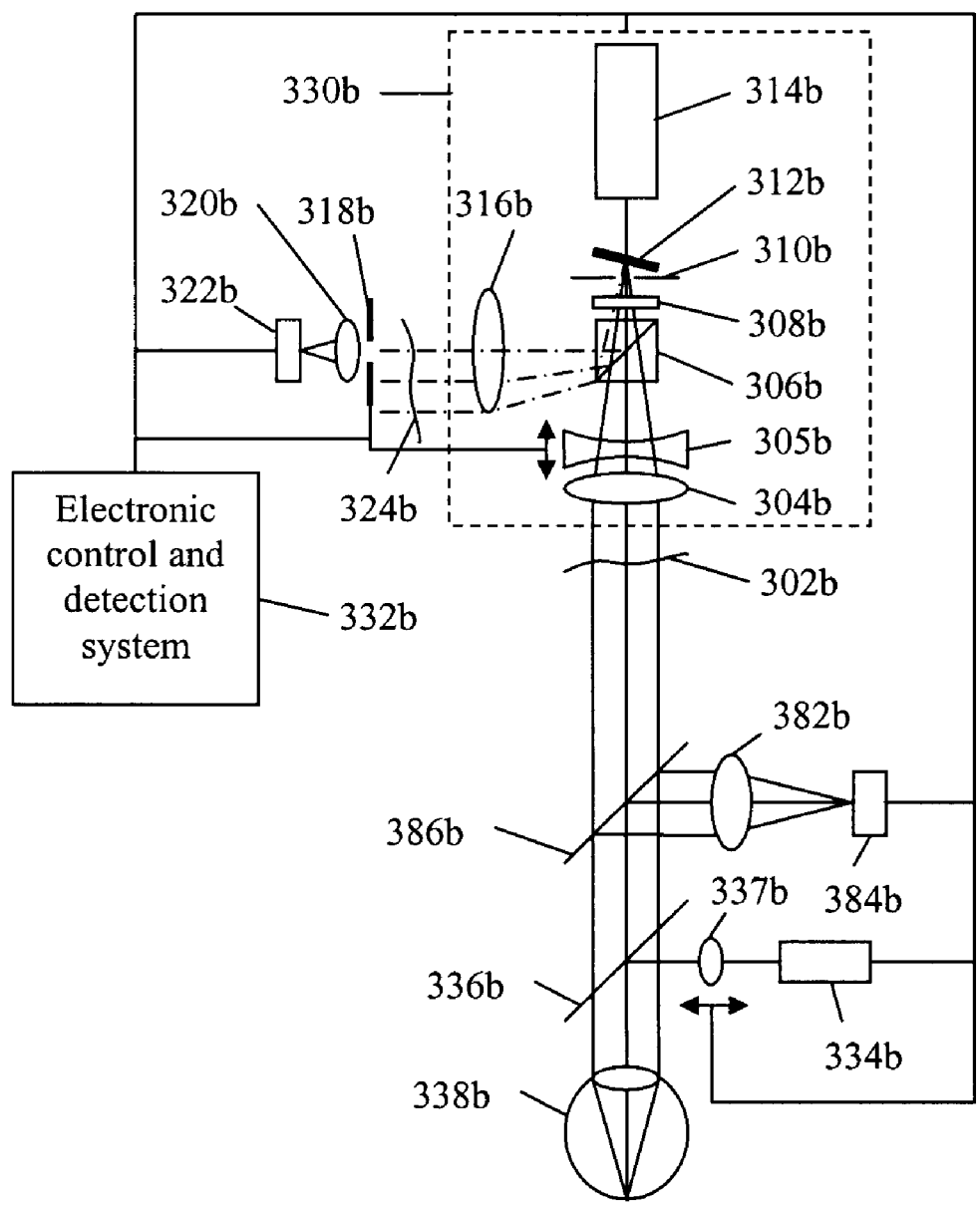
Figure 3C:
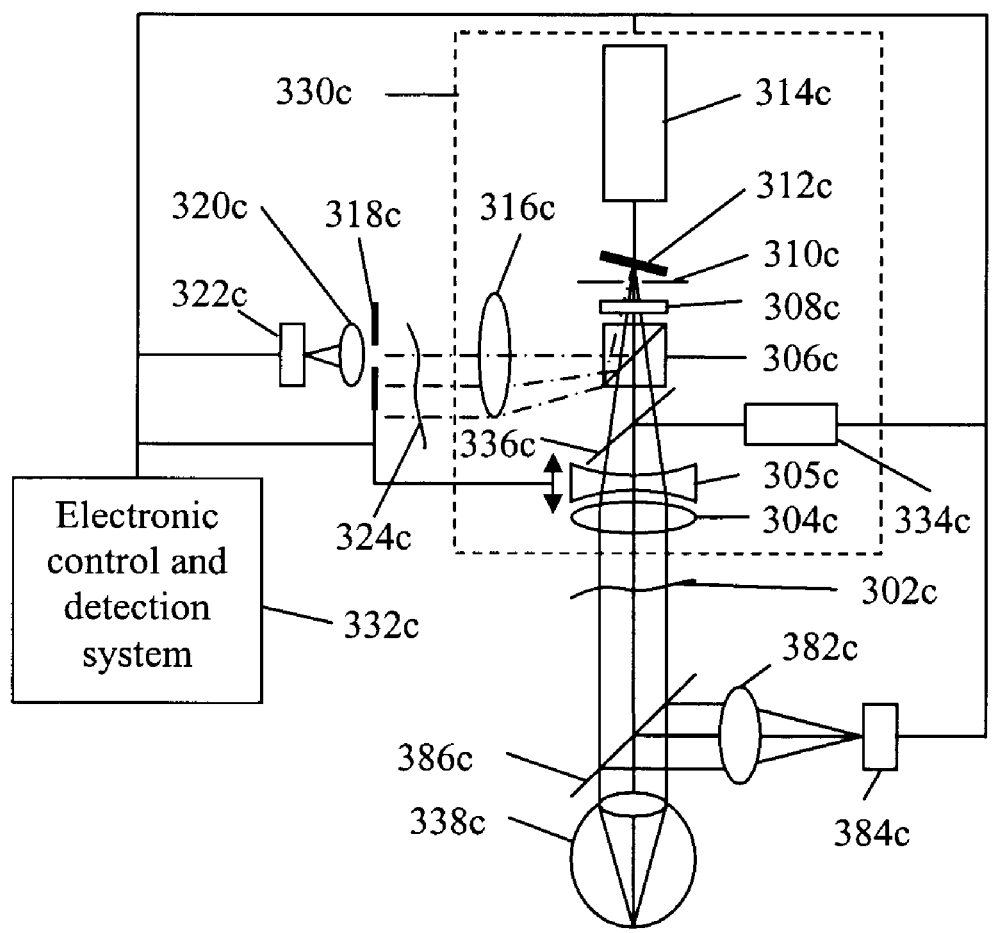

FIG. 3a, FIG. 3b, and FIG. 3c show some other embodiments in which the adaptive sequential wavefront sensor is used for measuring the wavefront from an eye. A narrow beam from a light source 334a 334b, 334c is directed to the eye retina through a beam directing element 336a 336b, 336c such as a mirror or a beam splitter. The wavefront from the eye is relayed by an objective lens 304a, 304b, 304c into a wavefront sensor as described in FIG. 2.

Here several variations in the optical layout are illustrated and discussed. In FIG. 3a, the light beam is projected from a point between the patient's eye and the objective lens 304a of the wavefront sensor. A focusing mechanism 337a is placed in the front of the light source 334a. Based on the pre-calibration data, real time measurement of wavefront error and eye accommodation, the focusing mechanism 337a can be used to maintain the focus of a narrow light beam onto the retina, resulting in a minimization of the measurement errors.

In the variation as shown in FIG. 3b, a focusing mechanism 305b is added to the objective lens 304b of the wavefront sensor, which can be used to calibrate the wavefront sensor to a known reference and can be operated independently from the focusing mechanism 337b being used for the input light beam. The focusing mechanism 337b functions in the same fashion as 337a in FIG. 3a.

In the optical arrangement illustrated in FIG. 3c, the objective lens 304c and the focusing lens 305c are shared by the projected narrow light beam and reflected wavefront from the eye. The focusing lens 305c not only is used to remove the defocus term from the wavefront sensor measurement, but also is used to maintain the focus of the projected light beam on the patient's retina.

An infrared (IR) camera 384a 384b, 384c can be combined with an IR imaging lens 382a, 382b, 382c and a beam splitter 386a, 386b 386c to monitor the position of the fovea. The same IR camera module can also be used for the alignment and registration of the eye.

Owing to the fact that the amount of light sent to an eye needs to be limited as required for safety reasons, the light source 334 (such as a superluminescent diode or SLD) is preferably operated in pulse and/or burst mode, and its operation in terms of the pulse turn-on time, duration and peak optical power or optical energy, is also coordinated or synchronized with the operation of the wavefront scanning module 330, the variable aperture 318, and the quadrant detector 322 under the control of the same electronic control and detection system 332. In other words, the light source will only be turned on for a short duration when the wavefront is scanned to the desired position, when the variable aperture is opened to the desired size, and when the detector is instructed to pick up the signal.

As mentioned before, a key advantage associated with the coordination of the variability of the aperture 318 with the wavefront scanning module 330, the light source 334 and the detector 322, is the capability to change the spatial resolution as well as the dynamic range of wavefront sensing in a synchronized way. For the case of a real eye, the higher order aberrations are more predominant in the outer or peripheral portion of the optical aperture. The varying sub-aperture and the larger dynamic range of the adaptive sequential wavefront sensor can be explored to cater for such demands. In particular, as the wavefront sensing sub-aperture is moved to the outer or peripheral region, the light source can be operated at a higher peak power and the size of the variable aperture opening can be reduced. This operation will provide a higher precision in terms of both spatial resolution and signal magnitude resolution because by increasing the light source power, the signal to noise ratio is also increased.

One challenge associated with a wavefront sensor for eye aberration measurement is that the safety requirement will put a limit to the amount of optical energy or peak power that can be delivered to the eye. A consequence of this limitation is that the signal to noise ratio of the detected wavefront signal may also be limited, which will translate to a limited light intensity resolution or detection limit. The use of a quadrant detector instead of a CCD or CMOS sensor will enable one to achieve a higher signal to noise ratio. In this respect, in addition to the inherently lower noise equivalent power of a quadrant detector as compared to a CCD or CMOS detector array, the use of a simple photo detector allows more sophisticated small signal detection schemes to be employed. Those proven techniques can significantly increase the light sensitivity for the wavefront sensor which often has very poor signal-to-noise input.

One example of the detection scheme is to have the light source modulated or operated in a burst mode to create a stream of light pulses, in which each pulse is then modulated by a carrier or modulation frequency at higher frequency. Accordingly, lock-in detection or synchronized detection can be utilized in the electronic circuitry to detect the intended light signal while suppressing the noise from the background. As an example, each photodiode channel of the four quadrant of the quad-detector can be arranged in an LC oscillation tank circuit that has a corresponding oscillation frequency the same as that used for modulating the light pulses. The circuitry can boost up the level of electronic signal even before the pre-amplifier stage. Alternatively, the electronic signal from each quadrant can be sampled at a frequency ten or more times higher than the modulation frequency, converted to a digital signal and then digitally filtered to achieve lock-in detection. Once converted to a digital signal, other digital signal extraction algorithms such as Kalman filtering can also be employed.

It should be understood that in addition to a normal eye, the eye examination for wavefront error or aberration can also be done pre and post refractive correction procedures. For example, the cornea might have undergone a refractive surgery such as LASIK (Laser-Assisted Stromal In-situ Keratomileusis), there might be an intraocular lens (IOL) already implanted in the eye or the eye might be wearing a contact lens or an ordinary spectacle lens. The presently disclosed adaptive sequential wavefront sensor potentially can be applied for characterizing the performance of these refractive correction procedures pre, intra and post the operation.

For example, in LASIK, the high speed adaptive sequential wavefront sensor can be used to provide monitoring of the wavefront correction as the corneal ablation is being done. In intraocular lens (IOL) implantation, the high speed adaptive sequential wavefront sensor can be used to indicate if the implanted IOL is positioned correctly in real time. In particular, for a multi-focal lens, be it in the form of a contact or an intraocular lens, the sub-wavefronts from different zones of the multi-focal lens will have different light focusing powers, and accordingly, the adaptive sequential wavefront sensor can be operated to sample the different zones with a correspondingly appropriate scanning pattern as well as a desired spatial resolution. Often, the optical surface of a multi-focal contact lens or a multi-focal intraocular lens is generally divided into a number of annular rings with each ring having a different focusing power. Generally, as the zone gets further away from the center and closer to the outer peripheral region, the width of the annular ring gets narrower. The variability of the presently disclosed adaptive sequential wavefront sensor is extremely suitable for sensing the different focusing powers of the different zones. The sub-wavefront aperture can be opened more for the central zone, and as the zone to be sensed moves to the outer regions, the sub-wavefront aperture opening can be reduced to a gradually smaller size to cater for the change in the width of each following zone's annular ring.

Figure 4:
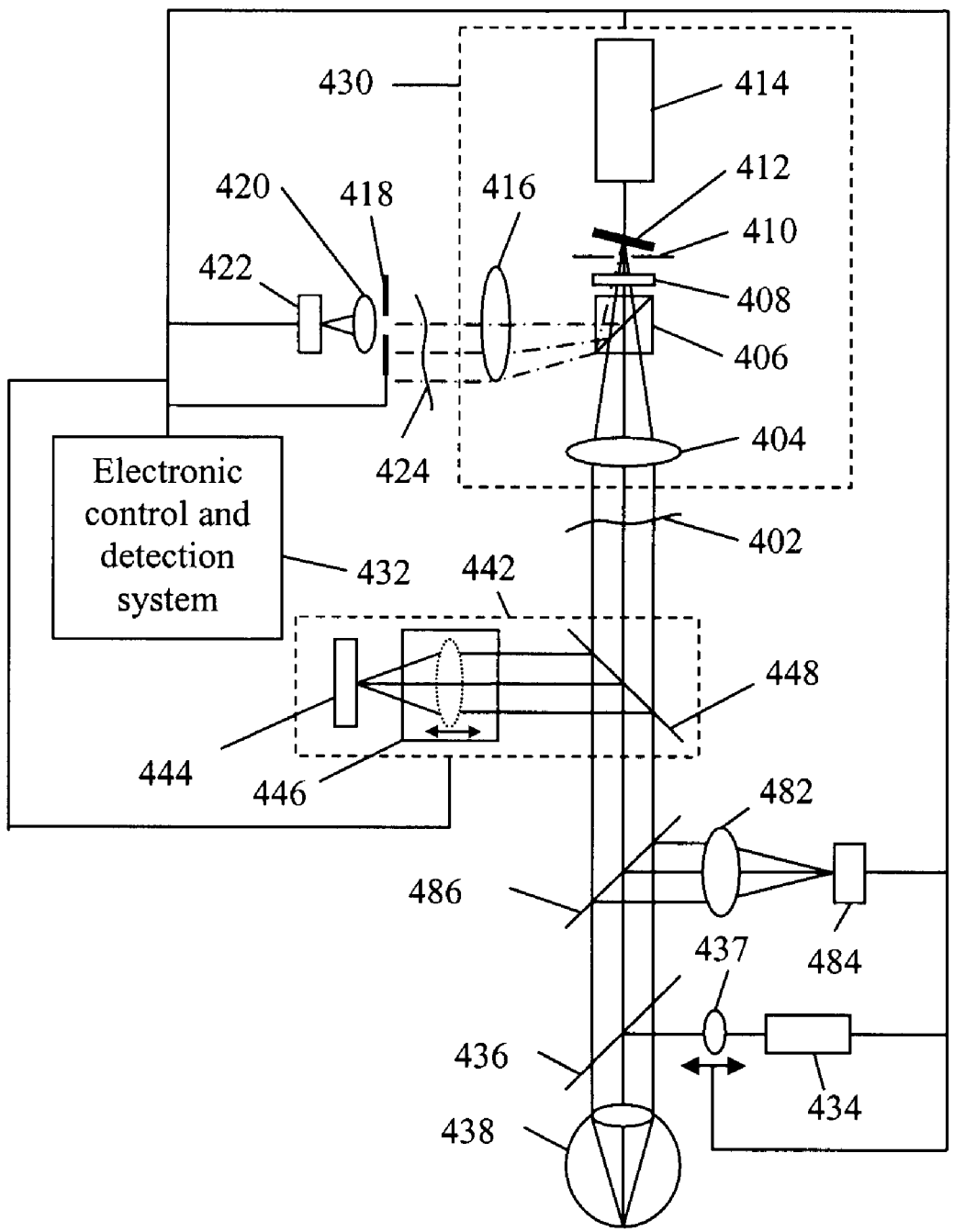
FIG. 4 shows an adaptive sequential wavefront sensor for sensing the wavefront from an eye in which a micro display based internal fixation and visual acuity projector module is added.

FIG. 4 shows another embodiment in which a micro display based internal fixation/visual acuity projector module is added to the system of FIG. 3a, FIG. 3b or FIG. 3c to enable additional functions that the adaptive sequential wavefront sensor can advantageously provide. The internal fixation module include a micro display target 444 which can also act as a visual acuity target projector, a focusing mechanism 446 (which can be constructed with an axially movable lens), and a beam splitter 448 that optically links the eye to the internal fixation/visual acuity projector module 442 for the eye's focusing on the micro display target. The focusing mechanism 437 is independently operated from the focusing mechanism 446 used for the input light beam. Based on the pre-calibration and real time measurement of wavefront error and eye accommodation, the focusing mechanism 437 is used to maintain the focus of a narrow light beam onto the retina, resulting in a minimization of the measurement errors.

A typical application of such a system, as shown in FIG. 4, is in auto-refraction measurement of eye. Traditional autorefractors are unable to do wavefront measurement, too slow to measure the dynamics of eye accommodation and they need additional subjective trial-and-error lens testing for prescription on a separate phoroptor.

The adaptive sequential wavefront sensor can be turned into an auto-refractor/wavefront sensor by operating the micro display target 444 as a programmable visual acuity projector. The focusing mechanism 446 can be operated to induce a change in the accommodation of the eye being examined and also to fog the eye. As the eye changes its accommodation, the instantaneous refractive errors and/or wavefront aberrations of the eye along a full accommodation range can be measured in real time. Such a measurement can thus provide information on the dynamics of accommodation, including the accommodation range or amplitude, the response speed of the eye's accommodation, and the associated instantaneous refractive errors or wavefront aberrations, the stabilized or dwelled refractive error, as well as higher order aberrations. One particular benefit that the adaptive sequential wavefront sensor can provide is the higher precision in determining the refractive errors. i.e. the sphero-cylinder errors, of the eye as wavefront measurement will be more accurate than a standard autorefraction measurement.

It is understood that the narrow light beam, as shown in FIG. 4, is projected from the point between the eye and beam splitter 448. In a practical application, various arrangements can also be implemented to achieve the same intended result. Examples have been provided in the configurations illustrated in FIG. 3b and FIG. 3c. The input light beam can also be projected into the fixation/target module first, going through or not through the focusing mechanism 446, and then into the eye through beam splitter 448.

It should be understood that other standard functions that are generally implemented for a standard auto-refractor can also be added to the system as shown in FIG. 4 to match the functionality. For example, near infrared illumination can be combined with a near infrared CCD camera together with some imaging lenses and dichroic mirror(s) to display a live image of the front portion of the eye such as the iris for an initial coarse alignment of the eye with respect to the auto-refractor/wavefront sensor. Such alignment system can provide tracking information for the orientation of the cornea, which, when combined with the location of iris, can be used as fiducial markers for the registration of optical reference plane. A near infrared light based automatic eye alignment mechanism can also be implemented as for a standard auto-refractor.

In addition, as mentioned in FIGS. 3a, 3b and 3c, an infrared (IR) camera 484 can be combined with an IR imaging lens 482 and a beam splitter 486 to monitor the position of the fovea. The same IR camera module can also be used for the alignment and registration of the eye. Furthermore, it can also be used to make sure that the patient is looking at the fixation light 444.

Figure 5:
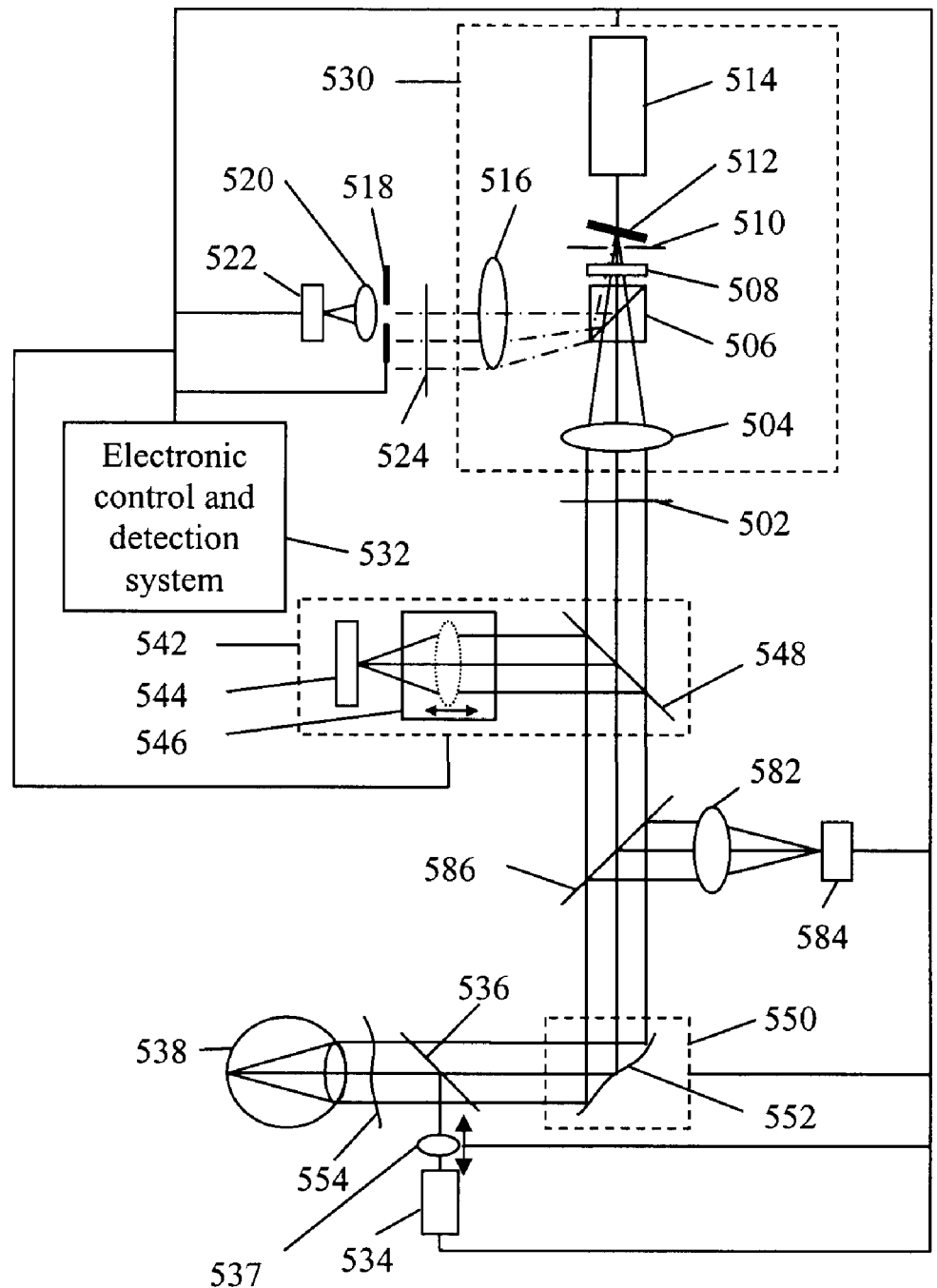
FIG. 5 shows an adaptive sequential wavefront sensor for sensing the wavefront from an eye in which a wavefront compensation module is added.

FIG. 5 shows another embodiment in which a wavefront compensation module is added to the adaptive sequential wavefront sensor to enable additional functions. The wavefront compensation module can be made from a deformable mirror 552. The real time adaptive sequential wavefront sensor can sense the overall input wavefront 502 and drive the deformable mirror 552 so that the aberrated wavefront 554 from the eye 538 can be fully or partially compensated by the wavefront compensation module 550.

One particular application of the configuration as shown in FIG. 5 is an integrated objective-subjective autorefractor. In such a case, the sub-wavefronts to be sampled can be selected around an annular ring of the input wavefront to the wavefront sensor, which will efficiently reveal the refractive errors as has been elaborated in the pending application entitled "SEQUENTIAL WAVEFRONT SENSOR" (application Ser. No. 11/335,980). At the same time, the micro display can be operated to fixate the eye to the desired distance and also programmed to display a visual acuity chart. Meanwhile, the wavefront compensation module can be activated to fully or partially compensate for the refractive error of the eye based on the measured wavefront errors.

The patient can be asked to read the visual acuity display to confirm that a desired visual acuity (for example 20/20) has been reached with the activated wavefront compensation. If not, the compensation can be fine tuned until the desired visual acuity is achieved. If only sphero-cylindrical error correction is desired instead of both low and high order corrections, the wavefront compensation module can be activated to only provide partial sphero-cylindrical compensations.

In this particular case, instead of using a high cost deformable mirror, an axially movable lens can be combined with a cylindrical aberration compensator, which can consist of two rotatable cylindrical lenses, to replace the deformable mirror to achieve the sphero-cylindrical compensations. The refractive correction that the wavefront compensation module provides does not need to exactly match the measured sphero-cylindrical aberrations and can be fine tuned around these measured values to also partially compensation the measured higher order aberrations so that the overall correction is optimized in spite of the fact that the correction is only in terms of sphero-cylindrical. Again, the patient can be asked in real time to read the visual acuity display to confirm that a desired visual acuity (such as 20/20) has been achieved with the activated sphero-cylindrical wavefront compensation and that he/she is comfortable with the correction.

The focusing mechanism 546 is used to introduce accommodation changes in a patient's eye to simulate the near side and far side vision conditions. The change in wavefront errors can be used to provide separate correction for near side and far side vision. During the process, the range or amplitude of accommodation and dynamics of accommodation, the difference in corrections obtained based on objective and subjective autorefraction are recorded for future study. The wavefront compensation, combined with the residual wavefront error measurement from the wavefront sensor, can be used to generate prescription for other vision correction means, including contact lens, LASIK procedure, IOL replacement, etc.

Such a new digital platform as an all-in-one instrument for lens prescription has a number of advantages when compared with the use of a standard autorefractor and a standard phoroptor. In addition to the fact that the new platform has both functions integrated into one instrument, the wavefront measurement can calculate both low and high order aberrations leading to higher precision lens prescription than a standard autorefractor; the integrated system is more compact with a smaller footprint compared with today's multiple instruments; the overall time taken to complete a lens prescription for a clinician will be drastically shortened; The micro display based programmable and focus-adjustable fixation target/visual acuity projector will enable real time detection for the amplitude and dynamics of eye accommodation as well as simultaneous objective and subjective refraction.

The focusing mechanism 537 is independently operated from the focusing mechanism 546. Based on the pre-calibration and real time measurement of wavefront error and eye accommodation, the focusing mechanism 537 can be used to maintain the focus of narrow light beam onto the retina, resulting in a minimization of the measurement errors. It is understood that the narrow input light beam, as shown in FIG. 5, is projected from the point between the eye and wavefront compensation module 550.

In a practical application, various arrangements can also be implemented to achieve the same intended result. Examples are provided in the configurations illustrated in FIG. 3b and FIG. 3c. The light beam can also be projected into the fixation/target module first, going through or not through the focusing mechanism 546, and then into the eye through beam splitter 548. The introduction of a focusing lens next to objective lens 504, in the same arrangement as illustrated in FIG. 3b, FIG. 3c, enables compensation for the defocus term in the wavefront sensor which a deformable mirror often cannot do.

One important application of the adaptive sequential wavefront sensor is to provide the prescription for a cornea laser ablation profile, the prescription for an intra ocular lens (IOL) be it phakic or non-phakic, and the prescription for a contact lens. However, in order to generate accurate prescriptions, the cornea surface profile must also be measured and with its measurement registered against reference of the wavefront measurement. Traditionally, wavefront measurement and corneal topography measurement are performed using two separate instruments. As a result, the alignment or registration between the two measured data maps becomes a main issue. The cylindrical aberration introduced by a misalignment could be mistakenly considered as an inherent cylindrical wavefront error, resulting in wrong prescription. These problems can be solved by integrating the two instruments into one.

Figure 6:
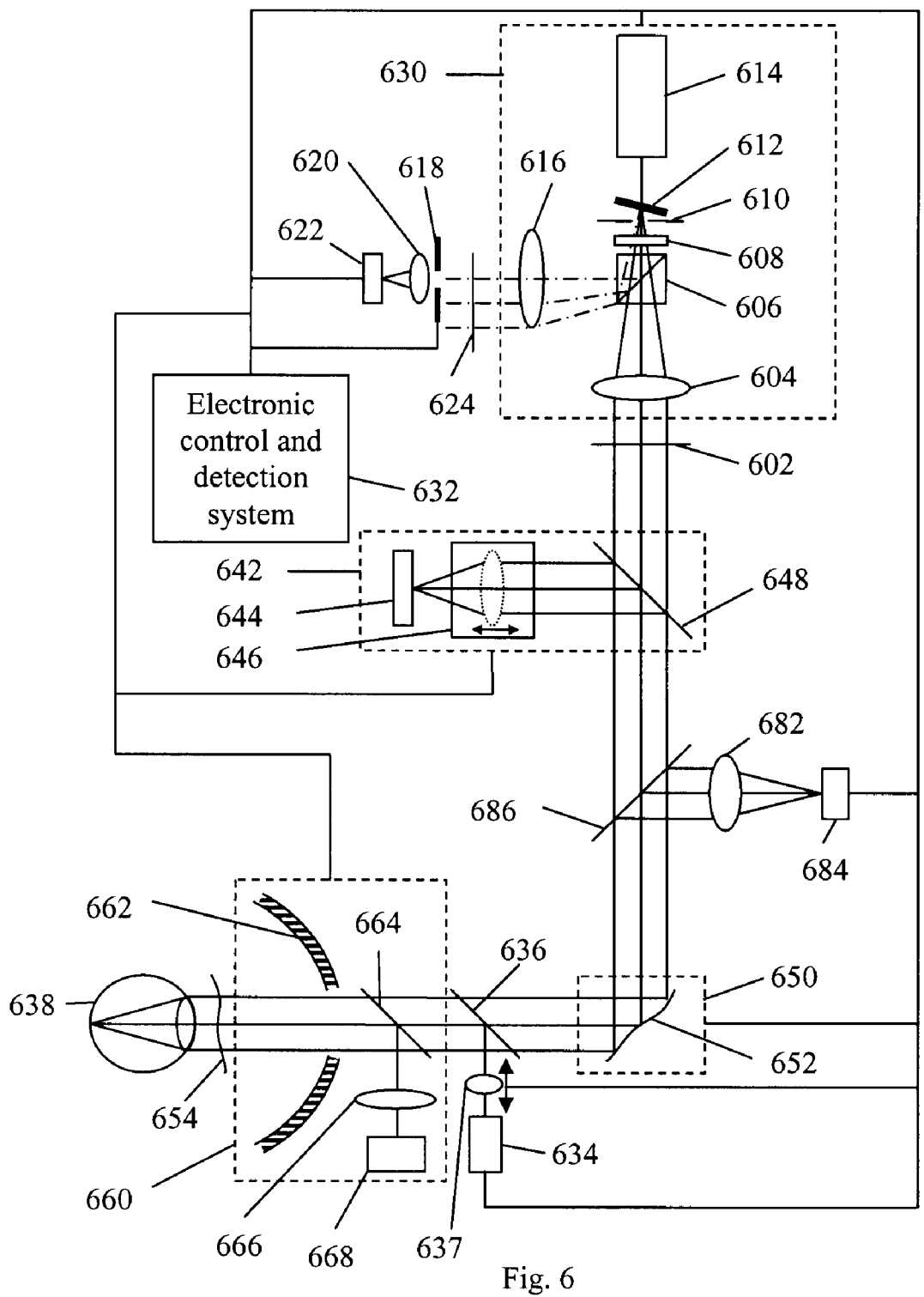
FIG. 6 shows an adaptive sequential wavefront sensor that is combined with a corneal topographer.

FIG. 6 shows an embodiment in which the adaptive sequential wavefront sensor based autorefractor, which is illustrated in detailed in FIG. 5, is combined with a corneal topographing device. The corneal topography module 660 can include a Placido disc 662, which is a series of illuminated concentric circles that are reflected off the cornea, a beam splitter 664, a lens 666 and an imaging camera 668. Since the concentric circles from the Placido disc 662 are imaged onto the imaging camera 668 through the reflection by the corneal surface and the refraction by lens 666, as is well known to those skilled in the art, as the corneal surface is not a perfect optical reflective element, the imaging camera captured circles will be distorted and the distortion will reveal the surface profile of the cornea under examination.

The integrated system shown in FIG. 6 has a number of advantages. The wavefront map and corneal topographic map are captured and generated simultaneously, or in a time sequential fashion but with such short separation so that the status of the eye is kept the same. In addition to the automatic alignment or registration between the captured topographic map of the cornea and the measured wavefront aberration map, the system is also more compact than two separate instruments.

A single internal fixation target or visual acuity projector 644 can be used for both measurements and this will ensure the same eye accommodation and iris dilation for both measurements. The measured corneal topographic map, when correlated with the position and other characteristics of the iris, including surface texture, could provide a unique and repeatable registration reference coordinate if the patient's eye is also fixated with the calibrated internal fixation light. This unique registration, when recorded with the patient's medical data can provide a reliable reference for future measurements, and reduce the inter-operative measurement errors associated with variations in reference points.

With the corneal surface profile map registered with the wavefront map, the use of the high speed adaptive sequential wavefront sensor will enable real time monitoring of the dynamics of eye lens accommodation by subtracting the contribution of cornea from the wavefront map for the whole ocular system, and the effect of iris dilation. The wavefront compensation module 650 can be activated to compensate for the eye aberration along with the change in the accommodation, and meanwhile a subjective confirmation of the refractive correction can also be obtained by projecting visual acuity target to the patient. When a desired eye accommodation is selected, the patient can be asked to confirm if a desired visual acuity is reached, once a final fine-tuned wavefront compensation that leads to a desired visual acuity has been reached, it can then be considered a preferred overall refractive prescription for the patient.

For the prescription for an intra ocular lens, the refractive focusing power of the cornea alone obtained through corneal topography measurement can be subtracted from the overall focusing power of the eye obtained from the wavefront measurement. For a contact lens, the corneal topography measurement will help in determining the profile of the posterior surface for the contact lens and the front surface profile of the contact lens can then be figured out with the help of the wavefront measurement. For LASIK, the corneal topography measurement can be combined with the wavefront measurement to give a prescription on the corneal ablation profile.

Since the wavefront sensor is operated in high speed, the topographer and the wavefront sensor can be operated sequentially to reduce interference between the two measurements. Alternatively, parallel measurements can be done by using light sources of different optical wavelengths, and with a dichroic beam splitter to combine the two optical paths. It should be understood that the corneal topographer shown in FIG. 6 is only for illustrative purpose. Other types of corneal topographer can also be used. For example, scanning optical slit based corneal topographer can also be used and in this apparatus, an additional advantage is added because the corneal thickness can also be mapped. Because the refractive power of the crystal lens of the eye alone can be calculated by subtracting the optical power of the cornea that can be obtained through the corneal topography and thickness measurement, from the overall focusing power of the eye that can be obtained through the wavefront measurement.

Other types of corneal topographers including those based on optical interferometry can also be used. Although the interferometry based corneal topographers may cost more, an advantage is their high precision in the measurement of the corneal surface profiles which may include both the anterior and the posterior surface and hence the corneal thickness map. The interferometric approach may also reveal more details of the optical characteristics of ocular system; and this information will be valuable for intra ocular lens prescription and implantation.

It is understood that the measured range and dynamics of accommodation, combined with the wavefront errors at various accommodation status for the ocular lens can provide much more accurate prescription for intra ocular lens replacement, in which the accommodation is adjustable by the patient once it is implanted. The same measurement, with registered reference, can be performed after the replacement operation, to confirm performance of the artificial lens, or to provide accurate prescription if additional fine tuning of the optical performance is required.

In addition to corneal topography, corneal thickness, and wavefront measurements, for precision intraocular lens (IOL) prescription and implantation, measurements of the biometry of the anterior chamber of the eye as well as the eye length are also preferred.

Figure 7:
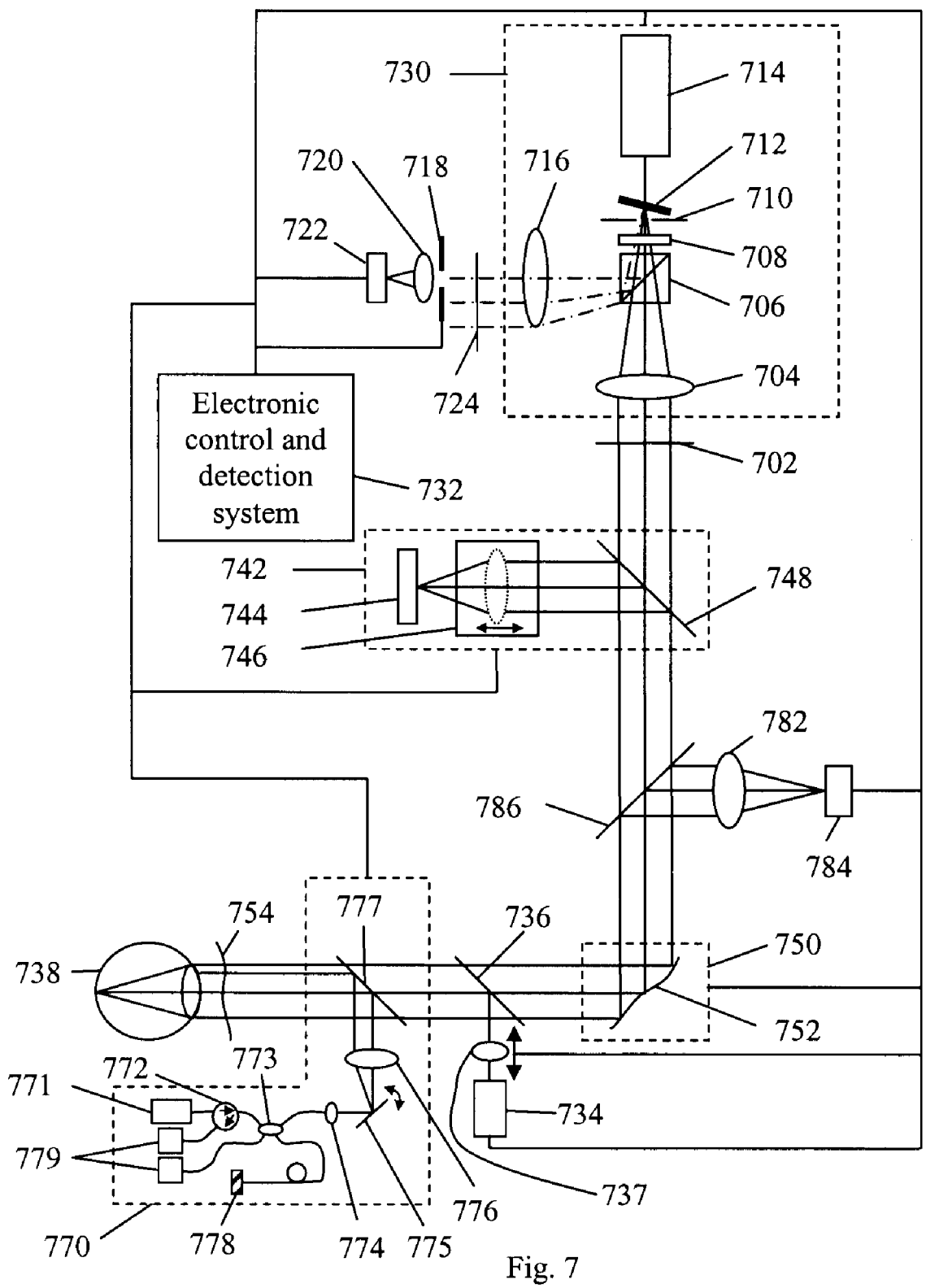
FIG. 7 shows an adaptive sequential wavefront sensor that is combined with an optical coherence tomography (OCT) module.

FIG. 7 shows another embodiment in which an optical coherence tomography (OCT) module 770 is integrated with the adaptive sequential wavefront sensor based autorefractor/aberrometer. Since an OCT module can provide relatively accurate measurement of many parameters of the eye, including the corneal surface profile, eye length and the anterior chamber biometry of the eye, the corneal topography module can be complemented or replaced by the OCT module. The OCT module is preferably a spectral domain OCT based system as it has a higher speed and also a higher sensitivity than a time domain based system. For example, the OCT module can be constructed using a tunable laser 771, a circulator 772, a 2×2 optical fiber coupler 773, a narrow beam collimator 774 to collimate the light from a fiber end, a two dimensional MEMS beam scanning mirror 775, a lens 776 to direct and focus the transversely scanned sample beam to the desired location of the eye, a dichroic mirror 777, a reference path reflection mirror 778, and a pair of detectors 779 for achieving balanced detection. The near infrared wavelength used for OCT can be different from that used for the adaptive sequential wavefront sensor. The OCT module can be dedicated for the measurement of the anterior part of the eye. It can also be used for measuring the eye length by introducing a step change in the reference path length when the OCT beam is scanned to the center of the eye. Note that although we have placed the OCT module before the wavefront compensation module because the OCT module is intended for measuring the anterior part of the eye, however, this should not limit the possibility of arranging the OCT module after the wavefront compensation module if the OCT module is to be used for measuring the retina of the eye, in which case, the wavefront compensation will result in a high transverse resolution of the OCT beam spot to the focus on the retina to provide super-resolution for the OCT image.

As for the case of corneal topographer integration, in the OCT integration case, a single internal fixation target or visual acuity projector 744 can be used for both OCT and wavefront measurements and this will ensure the same eye accommodation and iris dilation for both measurements. With the OCT generated map registered with the wavefront map, the use of the high speed adaptive sequential wavefront sensor will enable real time monitoring of the dynamics of eye accommodation and iris dilation. The wavefront compensation module 750 can again be activated to compensate for the eye aberration along with the change in the accommodation, and meanwhile a subjective confirmation of the refractive correction can also be obtained. When a desired eye accommodation is selected, the patient can be asked to confirm if a desired visual acuity is reached, once a final fine-tuned wavefront compensation that leads to a desired visual acuity has been reached, it can then be considered a preferred overall refractive correction for the patient. For the prescription for an intra ocular lens, the refractive focusing power of the cornea as well as other anterior chamber biometric parameters obtained through OCT measurement can be combined with the preferred overall refractive correction obtained from the wavefront measurement. The display of the information in real time related to the position and optical performance of the ocular after the implantation can help physician in making fine adjustment to the position of implant or the optical power/prescription of the implant to achieve the best performance. For a contact lens, the OCT measurement will help in determining the profile of posterior surface for the contact lens and the anterior surface profile of the contact lens can then be figured out with the help of the wavefront measurement. For LASIK, the OCT measurement can be combined with the wavefront measurement to give a prescription on the corneal ablation profile.

It must be noted that although in the illustrated embodiments, we have been adding modules to explain the additional functions that can be combined with the adaptive sequential wavefront sensor, however, these illustration should not limited the various possibilities of combining different module(s) with the adaptive sequential wavefront sensor. For example, the wavefront compensation module can be combined with the adaptive sequential wavefront sensor and a simple internal fixation target instead of a micro display based target can be used to accommodate the eye. Alternatively, the corneal topographer can be combined with the adaptive sequential wavefront sensor without the wavefront compensation module. Similarly, the OCT module can be combined with the adaptive sequential wavefront sensor without the wavefront compensation module. The adaptive sequential wavefront sensor can also be combined with all the modules, including the OCT module, the corneal topography module, the wavefront compensation module and the internal fixation/visual acuity projection module. There exist other possible combinations.

It should be re-emphasized that the presently disclosed high speed adaptive sequential wavefront sensor can be used for many applications. In addition to real time monitoring of the wavefront from an eye as the eye changes its accommodation and iris dilation, it can also be used for prescription of eyeglass lenses, contact lenses, intra ocular lenses and LASIK ablation profiles. These applications may require additional measurement of the eye and hence the presently disclosed adaptive sequential wavefront sensor can be integrated or combined with other instruments to accomplish the task. Furthermore, other benefits that the adaptive sequential wavefront sensor can provide, including the variability of the sub-wavefront aperture, the larger dynamic range, the synchronized operation of the various changeable elements, the adaptive sequential wavefront sensor can also be applied for many other applications, especially those that do not have a limitation on the optical power used, including astronomy, outer space imaging, optical lens or system characterization, optical alignment, and also military applications.

It should be understood that the description of the preferred embodiments of the invention are only for illustration purpose. Those skilled in the art may recognize other equivalent embodiments to those described herein; which equivalents are intended to be encompassed by the claims attached hereto.

What is claimed is:
1. An apparatus comprising:
an internal fixation/visual acuity projector module configured to project a selected pattern display;
a beam directing element configured to direct a portion of the selected pattern display towards a patient's eye;
a sub-wavefront focusing lens configured to focus a returned sub-wavefront to an image spot on a focal plane, with the returned sub-wavefront being a portion of a wavefront returned from the patient's eye, where the wavefront is generated by a light source with the light source being separate from the internal fixation/visual acuity projector module;

a sequential wavefront scanning device configured to sequentially shift the returned wavefront by a first displacement in a first dimension and a second displacement in a second dimension so that different portions of the wavefront are sequentially projected onto the sub-wavefront focusing lens;

a variable aperture configured to control the size of the sub-wavefront to be focused by the sub-wavefront focusing lens;

a position sensing device, located substantially at the focal plane of the sub-wavefront focusing lens, configured to indicate the two-dimensional displacement from a reference point of the image spot on the focal plane; and a controller, coupled to the variable aperture, scanning device, and internal fixation/visual acuity projector module, configured to coordinate the operation of the variable aperture, the scanning device and the internal fixation/visual acuity projector module.

2. The apparatus of claim 1, where the internal fixation/visual acuity projector module further comprises a focusing mechanism to induce change in accommodation or to fog the eye.

3. The apparatus of claim 1 with the controller configured to control the light source.

4. The apparatus of claim 1 with the controller configured to control the position sensing device.

5. The apparatus of claim 1 further comprising:

a wavefront compensation module positioned to fully or partially compensate an aberration of the sub-wavefront returned from the patient's eye.

6. The apparatus of claim 5 with the controller further configured to control the wavefront compensation module to fully or partially compensate for a refractive error of the patient's eye based on measured wavefront errors.

7. The apparatus of claim 5 further comprising:

a corneal topographing device configured to measure the corneal topography of the patient's eye and configured so that a corneal profile map is registered with wavefront measurements; and with the controller further coupled to the corneal topographing device and configured to coordinate the operation of the variable aperture, the scanning device, the internal fixation/visual acuity projector module, the wavefront compensation module and the corneal topographing device.

8. The apparatus of claim 5 further comprising: an optical coherence tomography (OCT) module configured to measure many parameters of the eye, including the corneal surface profile, eye length and the anterior chamber biometry of the eye and configured so that OCT module measurements are registered with wavefront measurements; and with the controller further coupled to the OCT and configured to coordinate the operation of the variable aperture, the scanning device, the internal fixation/visual acuity projector module, the wavefront compensation module and the OCT.

* * * * *